US012151109B2

(12) United States Patent
Austin et al.

(10) Patent No.: US 12,151,109 B2
(45) Date of Patent: Nov. 26, 2024

(54) IMPLANTABLE DEVICE COMPRISING A COIL ARRANGEMENT

(71) Applicant: BIOTRONIK SE & Co. KG, Berlin (DE)

(72) Inventors: Eric Austin, Portland, OR (US); Matthew Melius, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 515 days.

(21) Appl. No.: 17/431,605

(22) PCT Filed: Feb. 27, 2020

(86) PCT No.: PCT/EP2020/055110
§ 371 (c)(1),
(2) Date: Aug. 17, 2021

(87) PCT Pub. No.: WO2020/178123
PCT Pub. Date: Sep. 10, 2020

(65) Prior Publication Data
US 2022/0134096 A1   May 5, 2022

Related U.S. Application Data

(60) Provisional application No. 62/813,779, filed on Mar. 5, 2019.

(51) Int. Cl.
*A61N 1/362* (2006.01)
*A61N 1/05* (2006.01)
(Continued)

(52) U.S. Cl.
CPC ........... *A61N 1/362* (2013.01); *A61N 1/0587* (2013.01); *A61N 1/37229* (2013.01); *A61N 1/3756* (2013.01)

(58) Field of Classification Search
CPC .. A61N 1/362; A61N 1/0587; A61N 1/37229; A61N 1/3756
See application file for complete search history.

(56) References Cited

U.S. PATENT DOCUMENTS

| 8,903,497 | B2 | 12/2014 | Norgaard et al. | |
| 2015/0088221 | A1* | 3/2015 | Barr-Cohen | ........... A61N 1/059 607/9 |
| 2016/0151621 | A1 | 6/2016 | Maile et al. | |

FOREIGN PATENT DOCUMENTS

| WO | 2011130596 A1 | 10/2011 |
| WO | 2018094344 A2 | 5/2018 |
| WO | 2019036568 A1 | 2/2019 |

OTHER PUBLICATIONS

International Search Report (PCT/ISA/210) and Written Opinion (PCT/ISA/237) mailed on Jun. 4, 2020, by the European Patent Office as the International Searching Authority for International Application No. PCT/EP2020/055110.

* cited by examiner

*Primary Examiner* — Paula J Stice
(74) *Attorney, Agent, or Firm* — Buchanan Ingersoll & Rooney PC

(57) ABSTRACT

An implantable device comprises a housing having an oblong shape extending along a longitudinal axis, and a coil arrangement for communicating with an external device, the coil arrangement comprising a coil winding and a bobbin on which the coil winding is arranged. The coil arrangement is received in the housing such that the coil winding and the bobbin extend along a transverse direction with respect to the longitudinal axis, wherein the coil winding is wound on the bobbin about the transverse direction and has an elongated shape along the transverse direction.

14 Claims, 4 Drawing Sheets

(51) Int. Cl.
*A61N 1/372* (2006.01)
*A61N 1/375* (2006.01)

IMPLANTABLE DEVICE COMPRISING A COIL ARRANGEMENT

CROSS-REFERENCE TO RELATED APPLICATIONS

This application is the United States national phase under 35 U.S.C. § 371 of PCT International Patent Application No. PCT/EP2020/055110, filed on Feb. 27, 2020, which claims the benefit of U.S. Patent Application No. 62/813,779, filed on Mar. 5, 2019, the disclosures of which are hereby incorporated by reference herein in their entireties.

TECHNICAL FIELD

The present invention relates to an implantable device according to the preamble of claim 1.

BACKGROUND

An implantable device of this kind comprises a housing having an oblong shape extending along a longitudinal axis, and a coil arrangement for communicating with an external device, the coil arrangement comprising a coil winding and a bobbin on which the coil winding is arranged.

Such implantable device shall be configured for implantation into a patient, in particular into the heart of a patient. An implantable device in this context may for example be a pacemaker device, such as a leadless pacemaker, for providing for a pacing action in a patient's heart, or a defibrillator device, such as an implantable cardioverter-defibrillator (ICD), for providing for a defibrillation, or a monitoring device having a sensing function for monitoring for example a cardiac activity of a patient.

Implantable devices, in particular implantable devices which shall be directly implanted into the patient's heart, such as a leadless pacemaker, are small in size, relevant components of the device—such as an energy storage, a control circuitry and a communication unit—being encompassed in the housing in an encapsulated, fluid-tight fashion. A communication unit herein may provide for a communication with an external device, such as a programmer wand, to allow for a data exchange with an external device (for example for configuring the implantable device or for transferring information, such as monitoring data, to the external device) or for charging the implantable device in an implanted state.

Implantable medical devices, e.g. pacemakers or ICDs, usually have a coil for communication with an external programmer wand and/or for charging the device. Wire-wound coils for this purpose generally are well known in the field, as a means of low power inductive communication with an implanted medical device. In addition to air-core coils, various magnetic core materials (mu metal or ferrite cores) are also well known as a means to confine and guide a magnetic field for improved communication performance.

WO Publication No. 2011/130596 A1 discloses an arrangement for a partially implantable medical device in the shape of a cochlear implant system comprising a communications coil adapted for placement parallel to a corresponding partner coil for communication of an implant communication signal having an associated magnetic field component. An implant electronics module herein is adjacent to the communications coil and is electrically connected with it for coupling of the communications signal.

An implantable device such as a pacemaker device or a defibrillator device generally does not have a well-defined orientation when implanted into a patient's heart. A coil arrangement for providing for a communication with an external device, such as a programmer wand, herein shall allow for a robust, energy-efficient communication and in this respect shall be insensitive to variations in the orientation and placement of the implantable device. At the same time, due to the limited size of an implantable device such as a leadless pacemaker device or a defibrillator device, constraints may exist for the placement of the coil arrangement within the housing of the device.

The present disclosure is directed toward overcoming one or more of the above-mentioned problems, though not necessarily limited to embodiments that do.

SUMMARY

It is an object of the present invention to provide an implantable device allowing for an efficient operation, in particular for providing for a communication with an external device such as a programmer wand.

At least this object is achieved by means of an implantable device comprising the features of claim 1.

Accordingly, the coil arrangement is received in the housing such that the coil winding and the bobbin extend along a transverse direction with respect to the longitudinal axis, wherein the coil winding is found on the bobbin about the transverse direction and has an elongated shape along the transverse direction.

In particular, in one embodiment the coil winding may comprise a width measured along the transverse direction and a height measured along the longitudinal axis, wherein said width is larger than said height.

Generally, the coil winding, in a cross-sectional view in a plane perpendicular to the transverse direction, may have a circular or oval shape. The coil winding herein has an elongated shape in that its width along the transverse direction is larger than its height as measured along the longitudinal axis. Because the coil winding as well as the bobbin carrying the coil winding are oriented such that they extend along the transverse direction and hence transversely to the longitudinal axis, the coil arrangement with its coil winding and the bobbin may be received within the housing of the implantable device in an axially tight space, making it potentially possible to reduce the overall size of the implantable device, which may be beneficial for the implantation of the implantable device for example in a patient's heart and also to improve design options.

Due to the transverse extension of the coil winding and the bobbin with respect to the longitudinal axis of the implantable device the coil arrangement is configured to produce a predominantly magnetic field for an inductive coupling with a communication coil of an external device substantially at the lateral sides of the implantable device when viewed along the transverse direction. The bobbin herein may be shaped and configured such that a magnetic field distribution is achieved making a communication by inductive coupling with a communication coil of an external device insensitive to variations in the placement and orientation of the device when implanted in a patient, in particular a patient's heart.

In one embodiment, the coil winding comprises a first end and a second end, the first end and the second and being arranged on diametrically opposite sides of the longitudinal axis. The coil winding hence extends transversely to the longitudinal axis from one side of the longitudinal axis towards the other and has an elongated shape, such that a magnetic field distribution for an inductive coupling with an external communication coil is substantially produced at either side of the implantable device, when viewed along the transverse direction.

In one embodiment, the coil arrangement comprises at least one side face arranged at an end of the bobbin outside of the coil winding. The bobbin, with its end, protrudes from the coil winding. The side face is connected to or integrally formed with the bobbin such that it extends outside of the coil winding, the side face providing for a confinement and/or guiding of magnetic flux during operation of the coil arrangement for transmitting or receiving signals.

In a preferred embodiment, at each end of the bobbin a side face is formed, such that the bobbin at each end is terminated by a side face having a lateral extension exceeding the dimension of the bobbin (when viewed in a plane perpendicular to the transverse direction). The side faces hence protrude laterally from the bobbin, the side faces being shaped such that an improved distribution of the magnetic flux in operation of the coil arrangement is achieved, making the implantable device less sensitive to variations in the placement and orientation of the device when implanted into a patient.

The bobbin and side faces attached to the bobbin may in particular be fabricated from a ferromagnetic material, such that the bobbin may provide for a confinement and guiding of magnetic flux.

In one embodiment, the at least one side face is curved about the longitudinal axis. The at least one side face in particular may be shaped such that it comprises a curvature which is concentrical to the longitudinal axis, when viewed in a plane perpendicular to the longitudinal axis. The at least one side face hence has the shape of an arc extending about the longitudinal axis, the curvature of the at least one side face being defined by a (constant) radius with respect to the longitudinal axis.

In one embodiment, the housing comprises a chamber confined by an inner wall having a wall curvature in a plane perpendicular to the longitudinal axis. The coil arrangement herein is received within the chamber such that the coil arrangement is encompassed by the housing and is enclosed within the housing in a fluid-tight manner.

In one embodiment, the at least one side face arranged on the bobbin is curved such that it conforms to the wall curvature of the inner wall, when viewed in said plane perpendicular to the longitudinal axis. The shape of the at least one side face of the bobbin hence is adapted to the wall curvature of the inner wall of the chamber, such that the coil arrangement is received in the housing in a space-efficient manner.

The housing in particular may have a generally cylindrical, oblong shape with a substantially circular cross section. The at least one side face arranged on the bobbin hence conforms to the circular shape of the housing.

In one embodiment, the coil arrangement comprises a base plate having at least one termination pad for electrically connecting the coil arrangement to a circuitry of the implantable device. In particular, two termination pads may be arranged on the base plate, each termination pad being electrically connected to one winding end of the coil winding such that, by guiding a current via the termination pads, a current may flow through the coil winding for providing for a transmission or reception of signals or electrical energy by means of an inductive coupling to an external communication coil. The termination pads may allow for a connection of the coil arrangement to for example a circuit board structure, for example by applying a reflow soldering technique in the context of a surface mount assembly process.

In one embodiment, the coil winding and/or the bobbin are at least partially encapsuled by an overmolding material. The overmolding material may for example provide for an electrical insulation. The overmolding material may be formed for example on the base plate of the coil arrangement to enclose the coil winding, the bobbin and also side faces connected to the bobbin. The overmolding material hence may provide for an encapsulation of magnetically and electrically conducting components such as the coil winding, the bobbin and side faces connected to the bobbin. By encapsulating components of the coil arrangement by means of the overmolding material, a compact unit is produced which may be comfortably handled in particular when assembling the coil arrangement on a circuit board structure to be received within the housing of the implantable device.

In another embodiment, the coil winding and/or the bobbin is covered by a lid. In one embodiment, the lid has substantially the same shape and dimensions as the base plate, particularly in terms of the base area of the base plate. Accordingly, the lid may be arranged flush with the side faces of the coil arrangement. Preferably, the lid is made of a material, particularly a polymer, that is able to withstand conditions, particularly temperatures, of reflow soldering, e.g. not beyond 260° C., particularly between 240° C. and 250° C. Suitable materials for the lid include without being restricted to polymers used as substrate material for printed circuit boards, e.g. polyimides, liquid crystal polymers or FR4.

In one embodiment, the coil arrangement comprises a circuit board structure on which the coil arrangement is fastened. The circuit board structure in particular may comprise a mounting plate extending along a plane oriented perpendicularly to the longitudinal axis, the coil arrangement being fastened to the mounting plate. The mounting plate may have a generally circular shape such that it may be received within the chamber of the housing together with the coil arrangement placed thereon in a space-efficient manner.

In one embodiment, the circuit board structure comprises multiple mounting plates which extend along different planes oriented perpendicularly to the longitudinal axis. The mounting plates hence are displaced with respect to each other along the longitudinal axis, such that mounting plates on different levels with respect to the longitudinal axis are provided and received within the housing of the implantable device. On one of those mounting plates herein the coil arrangement may be fastened and electrically connected to the associated mounting plate. On another mounting plate electrical and electronic components, such as a control circuitry or an energy storage, may be received such that the circuit board structure provides for an assembly of a circuitry of the implantable medical device.

The coil arrangement may, for example, be received in between two neighboring mounting plates of the multiple mounting plates. The coil arrangement herein for example is mechanically and electrically fastened to one of the mounting plates, another mounting plate being arranged at a side opposite to the mounting plate to which the coil arrangement mechanically fastened and electrically connected.

In one embodiment, the circuit board structure comprises flexible connection sections, each flexible connection section connecting two neighboring mounting plates with each other. The circuit board structure may, in one embodiment, form a zig-zag shape (also denoted as "accordion" shape) in that a first mounting plate is connected via a first connection section at a first side of the longitudinal axis to a second mounting plate, and the second mounting plate is connected via a second connection section at a second side of the longitudinal axis opposite the first side to a third mounting plate. By means of further connection sections further mounting plates may adjoin the third mounting plate, such that multiple mounting plates by means of flexible connection sections are interconnected which each other and form a zig-zag (accordion) shape in that the connection sections are arranged on diametrically opposite sides with respect to the longitudinal axis in an alternating fashion.

The flexible connection sections may be formed by so-called flex-bands, such flex-bands providing for a mechanical interconnection as well as for electrical conduction paths in between neighboring mounting plates.

The mounting plates may be fabricated from a conventional, substantially rigid circuit board material such as FR4, a conducting-path structure being formed on each mounting plate for providing for a desired electrical function.

At least the object is also achieved by means of an implantable device comprising: a housing having an oblong shape extending along a longitudinal axis; and an electronic circuitry received in the housing. Herein, a circuit board structure is received in the housing and carries the electronic circuitry, wherein the circuit board structure comprises multiple mounting plates which extend along different planes oriented perpendicularly to the longitudinal axis and which are displaced with respect to each other along the longitudinal axis, wherein the circuit board structure forms a zig-zag shape in that a first mounting plate is connected via a first connection section at a first side of the longitudinal axis to a second mounting plate, and the second mounting plate is connected via a second connection section at a second side of the longitudinal axis opposite the first side to a third mounting plate.

The circuit board structure, on one of the mounting plates, in particular may carry a coil arrangement of the kind described above, such that it in this respect shall be referred to the above.

By equipping an implantable device with a circuit board structure having a zig-zag (or "accordion") shape comprising multiple mounting plates on which electrical or electronic components are received, a compact design of the implantable device becomes possible, allowing in particular for a space-efficient arrangement of a coil arrangement within the housing of the implantable device. The coil arrangement herein may be designed and configured such that a communication with an external device such as a programmer wand is comparatively insensitive to a placement and orientation when the device is implanted in a patient.

In a general aspect, an implant is provided which comprises a folded PCB (PCB printed circuit board), wherein the PCB is folded more than one time. The PCB may have zig-zag or accordion shape. In one embodiment, the PCB is folded three times. In this case, four mounting plates for receiving components are arranged parallel to each other, wherein the mounting plates are pairwise connected by three flex-bands.

In another aspect, an implant is provided with a coil arrangement, wherein the implant comprises a cylindrical housing having a longitudinal axis, wherein the coil arrangement comprises a bobbin and a coil, wherein the coil is disposed transverse to the longitudinal axis of the housing and wherein the coil extends across the longitudinal axis of the housing, e.g. such that a first end of the coil and a second end of the coil (which is opposite to the first end) are arranged on different sides of the longitudinal axis. The coil arrangement may comprise one or more (e.g. two) side faces which are configured to form a magnetic field generated by the coil. The side face(s) may be curved.

The implant may be a leadless pacemaker or a sensor, e.g. a pressure sensor.

In another aspect, a coil assembly is provided. The coil assembly comprises:
    a coil winding having an elongated cylindrical or oval shape and enclosing a cylindrical or oval interior area;
    a (e.g. ferromagnetic) bobbin, comprising: 1) a cylindrical or oval core providing a supporting surface for the coil winding and 2) an arrangement of larger opposing surfaces serving to focus and guide magnetic flux lines from a corresponding coil during an inductive communication session,
    whereas the opposing surfaces are shaped to capture magnetic flux lines even in the case of rotational misalignment of the two coils mentioned above.

In a further aspect, the coil assembly according to the above may be mounted on a PCB interposer configured with suitable termination pads for reflow soldering via a surface mount assembly process.

In yet another aspect, an implantable medical device is disclosed, the device comprising:
    a housing with a generally tubular/cylindrical cross section;
    a coil according to the above, accommodated within the housing;
    a coil according to the above, surface mounted an a PCB arranged in an accordion-like fold configuration such that the cylindrical axis of the coil is always perpendicular to the cylindrical axis of the device.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

Various features and advantages of the present invention may be more readily understood with reference to the following detailed description and the embodiments shown in the drawings. Herein.

DETAILED DESCRIPTION

Figure 1:
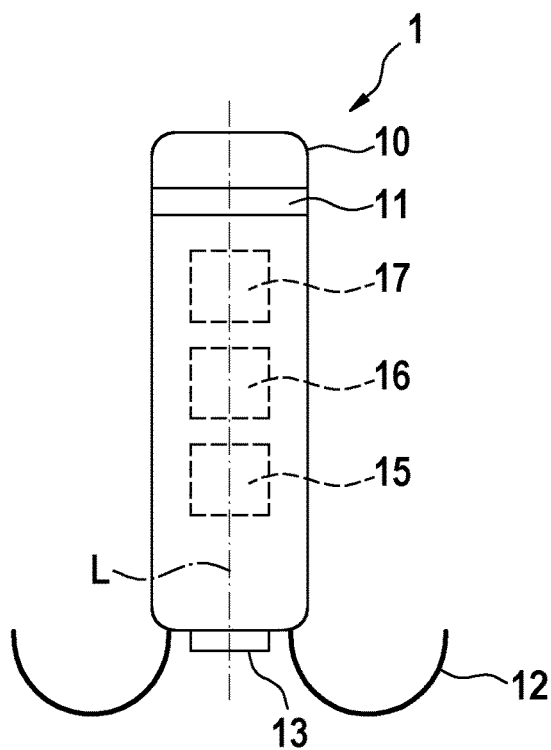
FIG. 1 shows a schematic illustration of an implantable intra-cardiac system.

Subsequently, embodiments of the present invention shall be described in detail with reference to the drawings. In the drawings, like reference numerals shall designate functionally similar structural elements, if appropriate.

It is to be noted that the embodiments are not limiting for the present invention, but merely represent illustrative examples.

FIG. 1 shows a schematic illustration of an implantable device 1 in the shape of an intra-cardiac pacing system (also denoted herein as implantable leadless pacemaker). The implantable device 1 comprises a housing 10 which encompasses an energy storage 17 (e.g. a battery), an electronic module 16, and a communication unit having a coil arrangement 15. The housing 10 may comprise titanium or may be made of titanium.

As visible from FIG. 1, the housing 10 of the implantable device 1 has a generally oblong, for example cylindrical shape extending along a longitudinal axis L.

At a distal end of the housing 10, a first electrode 13 (also called pacing electrode) is disposed. In a proximal region of the housing 10, a second electrode 11 (also called sensing electrode, which may also act as a return electrode for the pacing electrode) is arranged. The second electrode 11 may be formed as a ring electrode.

The implantable device 1 may be fixed to cardiac tissue by a fixation device 12. The fixation arrangement 12 may be formed by tines comprising Nitinol or being made of Nitinol. In one embodiment, four tines made of Nitinol may be formed at the distal end of the housing 10.

The energy storage 17 may be configured to provide electrical energy to the components of the implantable device 1, in particular to the electronic module 16, the coil arrangement 15, and the electrode arrangement of the first electrode 13 and the second electrode 11.

The electronic module 16 may be configured to perform the functions of a pacemaker, including sensing cardiac events and providing pacing pulses. The electronic module 16 may comprise a processor and memory.

The coil arrangement 15 may be configured for communication with an external device (e.g. a programmer wand). The coil arrangement 15 may be configured to inductively couple to an external communication coil for providing for a communication, as shall be explained further below.

In an implanted state, the implantable device 1, at its distal end, is placed on tissue, for example cardiac tissue of a patient's heart, such that the tines of the fixation device 12 engage with the tissue and the electrode 13 comes to rest on tissue such that it electrically contacts with the tissue. By means of the electrode arrangement formed by the electrodes 11, 13, hence, electrical energy may be injected into or delivered to the tissue for providing a stimulation, for example a pacing action or a defibrillation.

Figure 2:
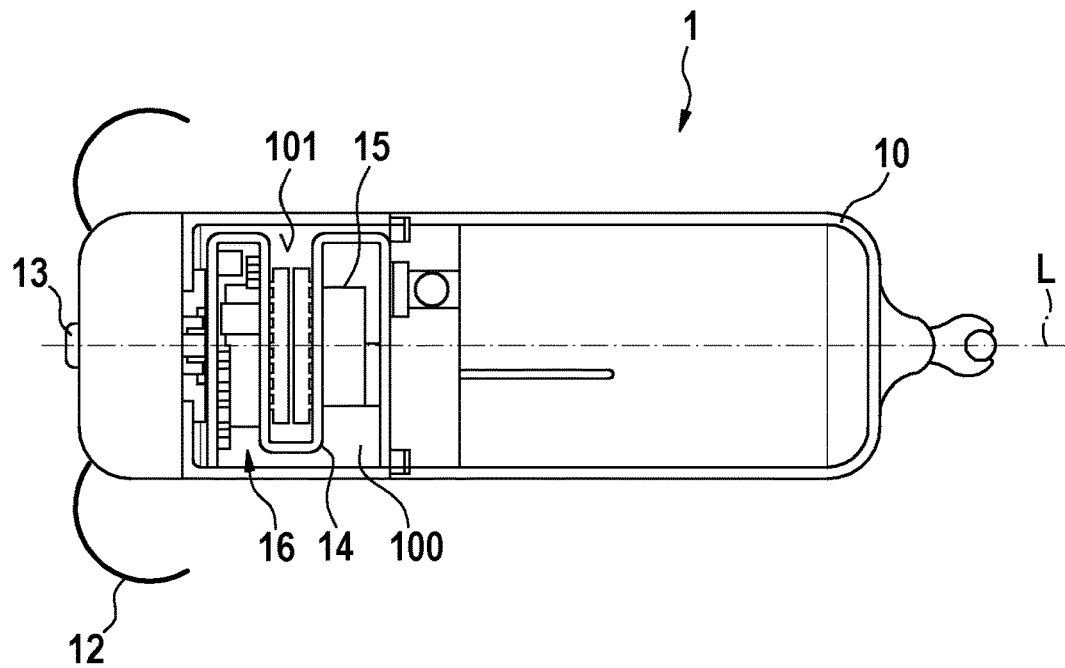
FIG. 2 shows a schematic illustration of another implantable intra-cardiac system.

Referring now to FIG. 2, an implantable device 1 in the shape of a leadless pacemaker comprises a housing 10, at a distal end of which a fixation device 12 having tines for fixing the device to cardiac tissue is arranged and an electrode 13 is disposed. The implantable device 1 may further comprise some or all components as described above in the context of FIG. 1, in particular an energy storage 17 and an electronic module 16.

Similarly to the embodiment of FIG. 1, in the embodiment of FIG. 2 the implantable device 1 has an oblong shape, the housing 10 of the implantable device 1 extending along a longitudinal axis L. The implantable device 1 may for example have the shape of a cylindrical capsule, the housing 10 having a length as measured along the longitudinal axis L substantially exceeding the diameter of the housing 10 as measured in a plane perpendicular to the longitudinal axis L.

Figure 3:
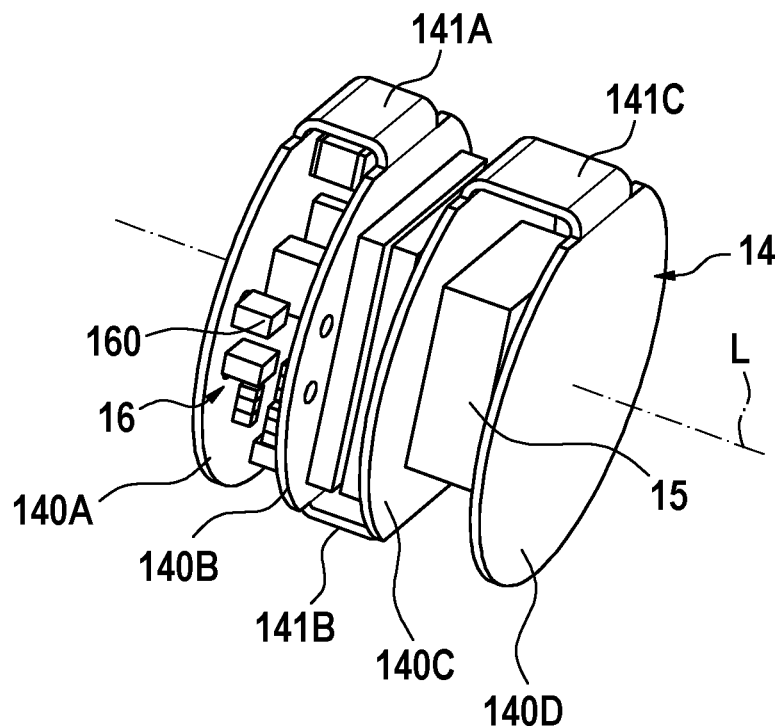
FIG. 3 shows a schematic illustration of a folded circuit board.

In the embodiment of FIG. 2, the implantable device 1 comprises a circuit board structure 14 comprising a flex-circuit printed circuit board (PCB) folded into a zig-zag ("accordion") shape, as illustrated in another view in FIG. 3. The circuit board structure 14 comprises multiple mounting plates 140A-140D which extend along parallel planes perpendicular to the longitudinal axis L and hence are offset with respect to each other along the longitudinal axis L. Neighboring mounting plates 140A-140D herein are connected to each other by flexible connection sections 141A-141C such that an interlinked circuit board structure 14 is formed carrying electrical and electronic components of the implantable device 1.

Within the circuit board structure 14, the zig-zag shape is formed in that the mounting plates 140A-140D are connected to each other by means of the connection sections 141A-141C in an alternating fashion at diametrically opposite sides with respect to the longitudinal axis L. In particular, a first mounting plate 140A carrying components 160 of an electronic module 16 is connected to a neighboring, second mounting plate 140B by means of a connection section 141A on a first side of the longitudinal axis L, as this is visible in FIG. 3. The mounting plate 140B is connected to a neighboring, third mounting plate 140C by means of an connection section 141B, the connection section 141B being formed at a side diametrically opposite, with respect to the longitudinal axis L, to the connection section 141A. The mounting plate 140C in turn by means of a connection section 141C is connected to another, fourth mounting plate 140D, the connection section 141C again being located at a side of the longitudinal axis L diametrically opposite to the connection section 141B, as visible from FIG. 3.

The connection sections 141A-141C may be formed by so-called flex-bands mechanically interconnecting the mounting plates 140A-140D. Conduction paths herein may be formed on the connection sections 141A-141C such that via the connection sections 141A-141C also an electrical interconnection in between the mounting plates 140A-140D is established.

The mounting plates 140A-140D each have a substantially circular shape, when viewed in an associated plane perpendicular to the longitudinal axis L of the implantable device 1. The circuit board structure 14 herein is received within a chamber 100 formed by the housing 10 and confined by an inner, cylindrical wall 101 surrounding the chamber 100. The shape of each mounting plate 140A-140D substantially conforms to the circular cross-sectional shape of the chamber 100, such that the circuit board structure 14 is received within the housing 10 in a space-efficient manner.

Because multiple mounting plates 140A-140D are stacked and displaced with respect to each other along the longitudinal axis L, electrical and electronic components may be received within the housing 10 in a space-efficient, stacked manner, allowing to design a compact implantable device 1 having reduced space requirements and an increased packing density.

Alternatively, the space being gathered by the increased space efficiency may be used to provide a device with, e.g., a larger battery capacity and thus greater longevity.

Electronic components 160 received on the mounting plate 140A may, for example, comprise a processor and a memory, for example in the shape of integrated circuits (ICs).

The implantable device 1 comprises a coil arrangement 15 arranged on the mounting plate 140C, the coil arrangement 15 being mechanically connected and electrically contacted to the mounting plate 140C. The coil arrangement 15 herein, as visible from FIGS. 2 and 3, is received in between the two neighboring mounting plates 140C, 140D. Alternatively, the coil arrangement 15 may be mechanically connected and electrically contacted to the mounting plate 140D.

Figure 4:
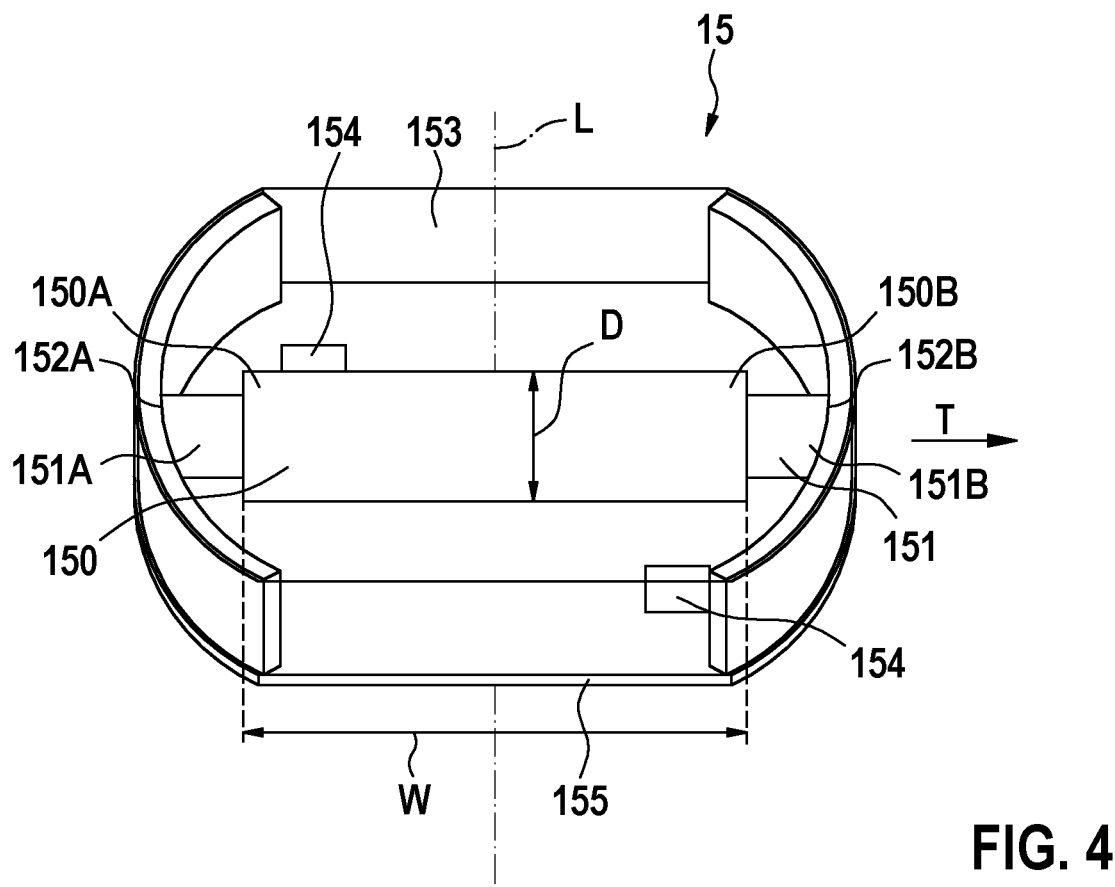
FIG. 4 shows an embodiment of a coil arrangement.

Referring now to FIG. 4, the coil arrangement 15 in one embodiment comprises a coil winding 150 and a bobbin 151, which together extend along a transverse direction T oriented at a perpendicular angle with respect to the longitudinal axis L of the implantable device 1. The coil winding 150 is wound about the transverse direction T on the bobbin 151, which is for example fabricated from a ferromagnetic material and hence forms a ferromagnetic core of the coil winding 150 for guiding and confining a magnetic flux to and from the coil winding 150.

As visible from FIG. 4, the coil winding 150 has an elongated shape in that, in one embodiment, the coil winding 150 comprises a width W along the transverse direction T which is substantially larger than a height D of the coil winding 150 as measured along the longitudinal axis L. The coil winding 150 herein may have a generally cylindrical shape, with a circular or oval cross-section when viewed in a cross-sectional plane perpendicular to the transverse direction T.

As in addition visible from FIG. 4, ends 150A, 150B of the coil winding 150 are placed at diametrically opposite sides with respect to the longitudinal axis L.

The bobbin 151 extends through the coil winding 150 and, with ends 151A, 151B, protrudes from the coil winding 150 at each end 150A, 150B of the coil winding 150. Each end 151A, 151B of the bobbin 151 herein carries a side plate 152A, 152B, each side plate 152A, 152B having a curved arc-shape, the curvature of which is concentrical to the longitudinal axis L.

By means of the curved side plates 152A, 152B the coil arrangement 15 conforms to the cylindrical inner wall 101 of the chamber 100 of the housing 10 such that the side plates 152A, 152B extend along the inside of the inner wall 101. The side faces 152A, 152B herein are shaped to provide for a guiding and confinement of magnetic flux to and from the coil winding 150, such that an improved magnetic field distribution M is achieved, as this is schematically illustrated in FIG. 6 (providing merely for a qualitative illustration of the magnetic field distribution M in the vicinity of the implantable device 1).

The coil arrangement 15 furthermore comprises a base plate 155 on which termination pads 154 are arranged for establishing a soldering connection to the associated mounting plate 140C. The termination pads 154 in particular allow for an assembly of the coil arrangement 15 on the mounting plate 140C making use of a reflow soldering technique in the context of a surface mount assembly process, as described in U.S. Pat. No. 8,694,101, which shall be incorporated in its entirety by reference herein.

In the embodiment of FIG. 4, the coil winding 150, the bobbin 151 and the side plates 152A, 152B are encapsulated by an overmolding material 153 (shown as transparent in FIG. 4 in order to allow for a view of the construction), the overmolding material 153 being electrically insulating.

Figure 5:
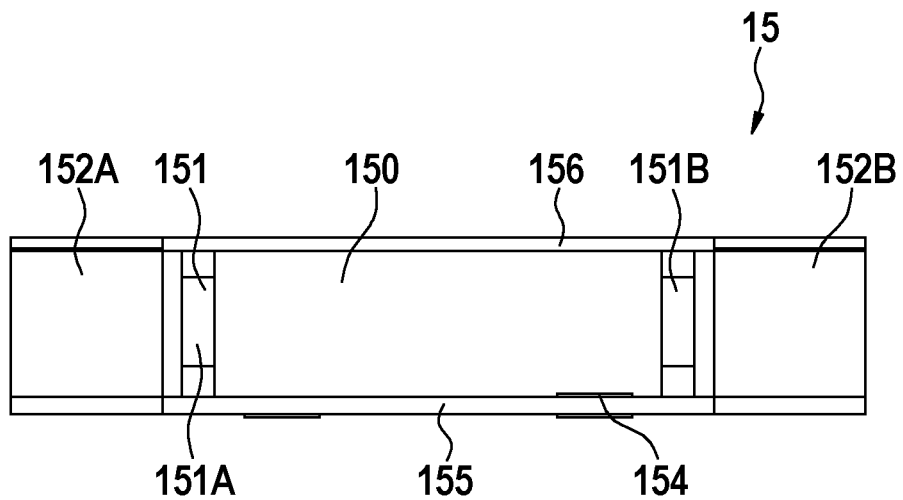
FIGS. 5-6 show an alternative embodiment of a coil arrangement.
Figure 6:
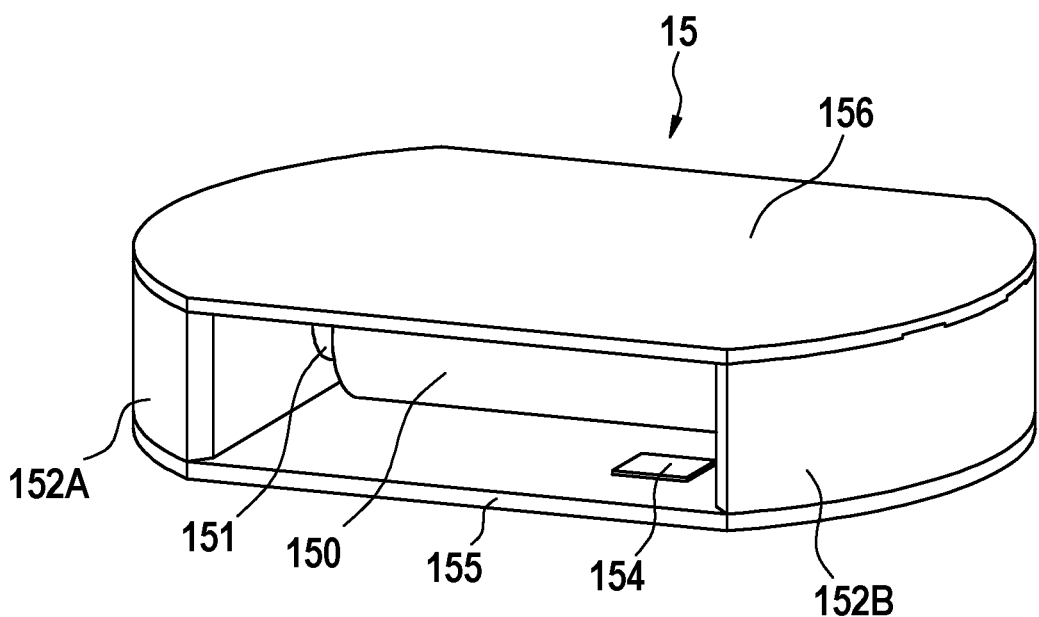

In an alternative embodiment, depicted in FIGS. 5 and 6, the coil winding 150, the bobbin 151 and the side plates 152A, 152B are covered by a lid or a cap 156 instead of encapsulated by an overmolding material as depicted in FIG. 4. The lid or cap 156 is preferably made of a polymer capable of withstanding conditions of surface mount reflow, e.g. 240° C. to 250° C. particularly surface mount reflow temperature. Suitable materials include without being restricted to polymers used in the manufacturing of printed circuit boards, such as polyimides or liquid crystal polymers. Preferably, the lid or cap 156 exhibits substantially the same shape and size as the base plate 155 of the claim arrangement 15.

Figure 7:
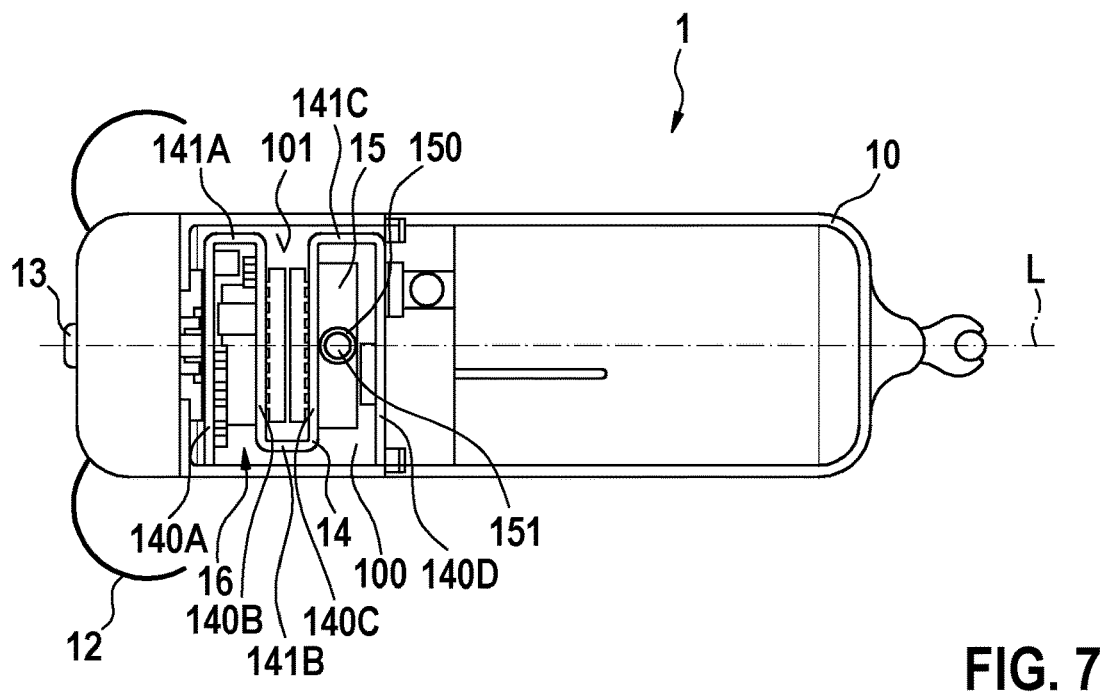
FIG. 7 shows yet another implantable intra-cardiac system.

Because the coil winding 150 has an elongated shape, the coil arrangement 15 may be of a flat design, as visible in FIGS. 4, 5 and 6, such that the coil arrangement 15 may be space-efficiently placed in between two neighboring mounting plates 140C, 140D, as illustrated in FIG. 7. The coil arrangement 15 in this way may be arranged such that it extends flatly in parallel to the mounting plates 140A-140D of the circuit board structure 14, the coil arrangement 15 being mechanically and electrically connected to an associated mounting plate 140C for providing an electrical communication function.

For an implantable device 1 having a generally cylindrical shape, such as a leadless pacemaker, the coil axis relative to the patient and/or programmer may not be well-defined, due to many variables in the implant assembly, delivery system, patient anatomy, and number of times the device is recaptured/repositioned. The coil arrangement 15 having a coil winding 150 and a bobbin 151 extending along the transverse direction T (and hence transversely across the longitudinal implantable device 1) and terminated by curved side faces 152A, 152B, offers advantages, including for example that the curved shape fits more efficiently within a cylindrical implantable device, leaving more space for the coil winding and terminations, and the curved side faces 152A, 152B gather and direct the magnetic flux lines more effectively than flat plates, making the coil less sensitive to rotational orientation of the implantable device 1.

Figure 8:
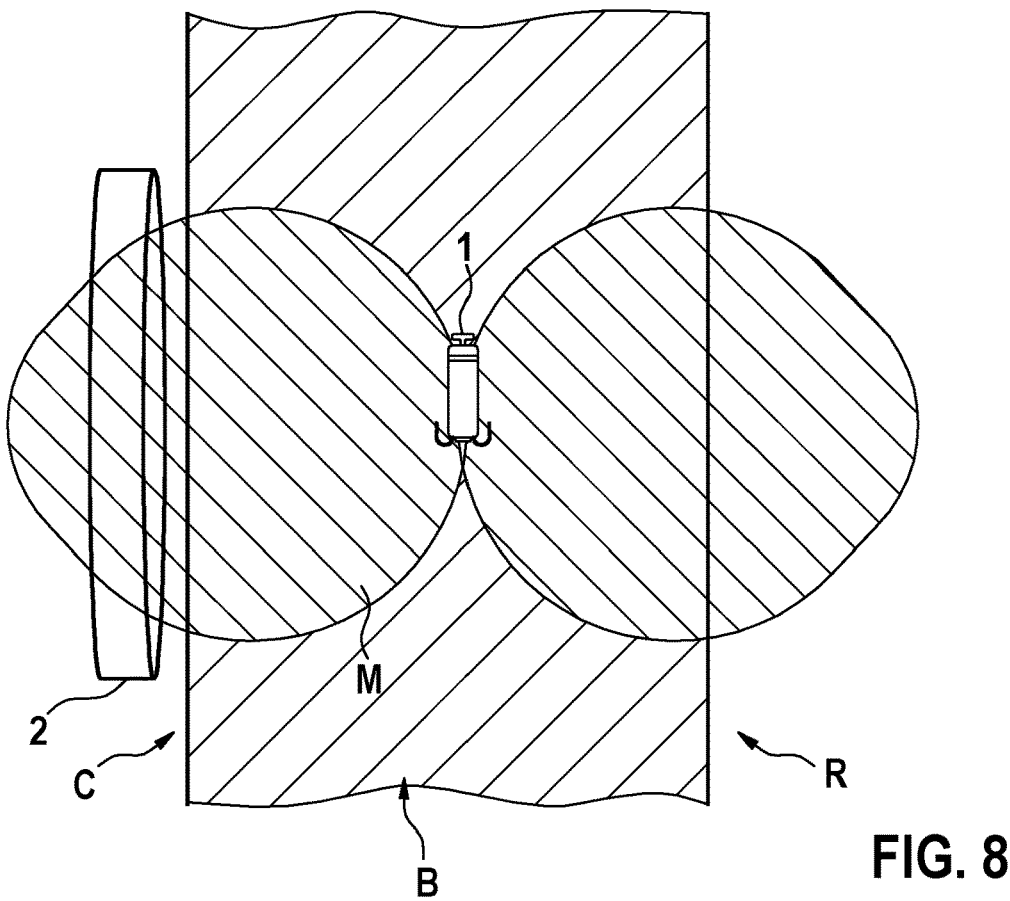
FIG. 8 shows a qualitative illustration of a magnetic field distribution of the system according to FIG. 7.

As visible from the schematic illustration of FIG. 8, due to the orientation of the coil winding 150 and the bobbin 151 and in addition due to the formation of the side plates 152A, 152B, magnetic field lobes M indicative of a field distribution for transmission as well as for a field sensitivity for reception are formed at lateral sides of the implantable device 1 such that an inductive coupling to an external device 2 having an inductive communication coil is comparatively insensitive to a placement and orientation of the implantable device 1 in a patient's body B. The external device 2 herein may be placed in the vicinity of the patient's chest C (or alternatively in the vicinity of the patient's back R), the external device 2 being enabled to inductively couple to the coil arrangement 15 of the implantable device 14 for exchanging data with the implantable device 1 or for providing for a charging of the implantable device 1 by an inductive transfer of energy.

The embodiments disclosed herein may have one or more of the following advantages:

First, a more robust and reliable wand/implant communication architecture employing an optimized coil design which may exhibit the following advantages:
    improved physician and patient experience due to:
        improved coil-to-coil coupling, i.e., less sensitivity to alignment of the implant and programming wand, and increased programming distance,
        potentially shorter office visits during follow-up, etc. due to improved performance,
    increased device longevity due to the above efficiencies resulting in much shorter communication sessions and therefore less battery drain.

Second, the coil in combination with the accordion PCB may be more space efficient, providing for the following possibilities:
    a smaller device size
        easier to implant due to better navigation of patient's anatomy,
        takes up less volume in the heart,
        more placement flexibility for optimal positioning within the heart, space allocation to other features
    future therapies,
    larger battery for increased device longevity.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 Implantable device (pacemaker device)
10 Housing
100 Chamber
101 Inner wall
11 Electrode
12 Fixation device
13 Electrode
14 Circuit board structure
140A-140D Mounting plate
141A-141C Connection sections (flex-bands)
15 Coil arrangement
150 Coil winding
150A, 150B End of the coil
151 Bobbin
151A, 151B End of the bobbin
152A, 152B Side faces
153 Overmolding material
154 Termination pads
155 Base plate
156 Lid or cap
16 Electronic circuitry
160 Electronic components
17 Energy storage
2 Programmer wand
B Body
C Chest
D Height
L Longitudinal axis
M Magnetic field
R Back
T Transverse direction
W Width

The invention claimed is:

1. An implantable device, comprising:
a housing having an oblong shape extending along a longitudinal axis; and
a coil arrangement for communicating with an external device, the coil arrangement comprising:
    a coil winding and a bobbin on which the coil winding is arranged, wherein the coil arrangement is received in the housing such that the coil winding and the bobbin extend along a transverse direction with respect to the longitudinal axis, wherein the coil winding is wound on the bobbin only in the transverse direction and has an elongated shape along the transverse direction; and
    at least one side plate arranged at an end of the bobbin outside of the coil winding and wherein the side plate has a lateral extension exceeding a dimension of the bobbin when viewed in a plane perpendicular to the transverse direction.

2. The implantable device of claim 1, wherein the coil winding comprises a width measured along the transverse direction and a height measured along the longitudinal axis, wherein said width is larger than said height.

3. The implantable device of claim 1, wherein the coil winding comprises a first end and a second end, the first end and the second end being arranged on opposite sides of the longitudinal axis.

4. The implantable device of claim 1, wherein the at least one side plate is curved about the longitudinal axis.

5. The implantable device of claim 1, wherein the housing comprises a chamber confined by an inner wall having a wall curvature in a plane perpendicular to the longitudinal axis, wherein the coil arrangement is received within the chamber and the at least one side plate in said plane perpendicular to the longitudinal axis conforms to the wall curvature of the inner wall.

6. The implantable device of claim 1, wherein the coil arrangement comprises a base plate having at least one termination pad for electrically connecting the coil arrangement to a circuitry of the implantable device.

7. The implantable device of claim 1, wherein the coil winding and/or the bobbin are at least partially encapsuled by an overmolding material or covered by a lid.

8. The implantable device of claim 1, wherein the coil arrangement comprises a circuit board structure on which the coil arrangement is fastened.

9. The implantable device of claim 8, wherein the circuit board structure comprises a mounting plate extending along a plane oriented perpendicularly to the longitudinal axis, the coil arrangement being fastened to the mounting plate.

10. The implantable device of claim 8, wherein the circuit board structure comprises multiple mounting plates which extend along different planes oriented perpendicularly to the longitudinal axis and which are displaced with respect to each other along the longitudinal axis.

11. The implantable device of claim 10, wherein the coil arrangement is received in between two neighbouring mounting plates of the multiple mounting plates.

12. The implantable device of claim 10, wherein the circuit board structure comprises flexible connection sections, each flexible connection section connecting two neighbouring mounting plates with each other.

13. The implantable device of claim 10, wherein the circuit board structure forms a zig-zag shape in that a first mounting plate is connected via a first connection section at a first side of the longitudinal axis to a second mounting plate, and the second mounting plate is connected via a second connection section at a second side of the longitudinal axis opposite the first side to a third mounting plate.

14. The implantable device of claim 1, comprising: a circuit board structure received in the, wherein the circuit board structure comprises multiple mounting plates which extend along different planes oriented perpendicularly to the longitudinal axis and which are displaced with respect to each other along the longitudinal axis, wherein the circuit board structure forms a zig-zag shape in that a first mounting plate is connected via a first connection section at a first side of the longitudinal axis to a second mounting plate, and the second mounting plate is connected via a second connection section at a second side of the longitudinal axis opposite the first side to a third mounting plate.

* * * * *